United States Patent [19]

Lattin et al.

[11] 4,406,658
[45] Sep. 27, 1983

[54] IONTOPHORETIC DEVICE WITH REVERSIBLE POLARITY
[75] Inventors: Gary A. Lattin, Forest Lake; Richard Spevak, Minneapolis, both of Minn.
[73] Assignee: Medtronic, Inc., Minneapolis, Minn.
[21] Appl. No.: 241,284
[22] Filed: Mar. 6, 1981
[51] Int. Cl.³ .............................................. A61N 1/30
[52] U.S. Cl. .............................. 604/20; 128/419 R; 128/802
[58] Field of Search .......... 128/207.21, 419 R, 420 R, 128/783, 798, 802, 803, 639–641; 604/20

[56] References Cited

U.S. PATENT DOCUMENTS

| | | | |
|---|---|---|---|
| 2,784,715 | 3/1957 | Kestler | 128/207.21 |
| 3,215,139 | 11/1965 | Dietz | 128/207.21 |
| 3,699,263 | 10/1972 | Zaffaroni | 128/268 |
| 3,955,583 | 5/1976 | Horauf | 128/420 R |
| 4,019,510 | 4/1977 | Ellis | 128/207.21 |
| 4,125,110 | 11/1978 | Hymes | 128/641 |
| 4,141,359 | 2/1979 | Jacobsen | 128/207.21 |
| 4,209,020 | 6/1980 | Nielsen | 128/640 |
| 4,230,010 | 10/1980 | Harwood | 128/156 |
| 4,250,878 | 2/1981 | Jacobsen et al. | 128/207.21 |
| 4,301,794 | 11/1981 | Tapper | 128/207.21 |
| 4,317,457 | 3/1982 | Guillot | 128/802 X |

FOREIGN PATENT DOCUMENTS 706092 12/1979 U.S.S.R. ........................ 128/207.21

OTHER PUBLICATIONS

"Painless Anesthesia" by Yvonne Baskin in Medical Electronics, Sep. 1979, pp. 60 & 61.
"Iontophoretic Local Anesthesia for Conjunctional Surgery" by Hampson A. Sisler, M. D. in Annals of Opthalmology, vol. 10, 1978, pp. 597 & 598.
"Iontophoresis-A Major Advancement", Editorial in the Eye, Ear, Nose and Throat Monthly, vol. 55, Feb. 1976, pp. 13 & 14.
"Treatment of Orthopaedic Infections with Electrically Generated Silver Ions" by Robert O. Becker and Joseph A. Spadaro, in The Journal of Bone and Joint Surgery (American Volume) Vo. 60-A, No. 7, Oct. 1978, pp. 871-881.
"Techniques for Iontophoresis" Letter by Charles M. Magistro and response by Joseph Kahn in Physical Therapy, vol. 57, No. 10, Oct. 1977, pp. 1193 & 1194.
"Iontophoresis-The Non-Invasive Administration of Drugs", Sales Brochure of Motion Control, Inc., 1005 South 300 West, Salt Lake City, Utah 84101, Form No. MC1 009-2/79.
"Phoresor-Iontophoretic Drug Delivery System-Instructions", Instruction Sheet distributed by Motion Control, Inc., 1005 South 300 West, Salt Lake City, Utah 84101, Form No. MC10017-6/79.
"Acetic Acid Iontophoresis for Calcium Deposits by Joseph Kahn in Physical Therapy, vol. 57, No. 6, Jun. 1977, pp. 658 and 659.
1978 Corporate Report of ALZA Corporation, pp. 1–11, available from ALZA Corp., 3170 Porter Dr., Palo Alto, Calif. 94304.
Sales Brochure distributed by Medco Products, Inc., 3601 East Admiral Place, Tulsa, Oklahoma 74115, Form No. HV 103673, Jun. 1979, 5 pages.
"Iontophoresis"-An excerpt from an article in the Journal of the New York State Society of Physiotherapists, Inc., Annual Issue, Jun., 1959, by Arthur Kahn and Joseph Kahn with updated material (received from Medco Products Co., Inc.).
"D.C. (Galvanic) Current"-Information Sheet distributed by Medco Products Co., Inc., 3601 East Admiral Place, Tulsa, Oklahoma 74115.
"Electro-Diagnosis"-Information Sheet No. 6301152, Distributed by Medco Products Co., Inc., 3601 East Admiral Place, Tulsa, OK 74115.
Levit, "Simple Device for Treatment . . . ", Archives of Dermatology, vol. 93, Nov. 1968, pp. 505-507.

Primary Examiner—Lee S. Cohen
Attorney, Agent, or Firm—Reed A. Duthler; John L. Rooney; Joseph F. Breimayer

[57] ABSTRACT

An iontophoretic device in which the polarity of the electrodes is reversible. There is a current source and a pair of electrodes. A polarity control between the current source and the electrodes determines the direction of current flow through and between the electrodes. A timer circuit communicates with the current source and the polarity switching circuit to automatically ramp down the current, switch polarity and then ramp up the current after the polarity has been switched, thereby permitting the iontophoretic process to take place under both electrodes with one application.

13 Claims, 6 Drawing Figures

IONTOPHORETIC DEVICE WITH REVERSIBLE POLARITY

BACKGROUND OF THE INVENTION

1. Field of the Invention

This invention in general relates to the field of iontophoretic introduction of ionic substances into a body, and more particularly concerns an iontophoretic device in which the polarity of the electrodes is reversible, thus providing an iontophoretic instrument with a doubled capacity and improved performance capabilities.

2. Description of the Prior Art

Iontophoresis is a method for introducing ionic substances into a body. The method utilizes direct electrical current to drive the ionized substances, such as chemicals or drugs, through the intact skin or other body surface. This has proven to be useful in numerous medical applications. U.S. Pat. No. 3,991,755 issued to Jack A. Vernon, et al and U.S. Pat. No. 4,141,359 issued to Stephen C. Jacobsen, et al. disclose examples of iontophoretic devices and some applications of the devices. The iontophoresis process has been found to be useful in the administration of lidocaine hydrochloride, hydrocortisone, acetic acid, flouride, penicillin, dexamethasone sodium phosphate and many other drugs. Perhaps the widest use of iontophoresis is that of diagnosing cystic fibrosis by using pilocarpine nitrate iontophoresis. The pilocarpine nitrate stimulates sweat production; the sweat is collected and analyzed for its chloride content to detect the presence of the disease.

In iontophoretic devices two electrodes are used. One electrode, called the active electrode, is the electrode at which the ionic substance is driven into the body. The other electrode, called the indifferent or ground electrode, serves to close the electrical circuit through the body. For example, if the ionic substance to be driven into the body is positively charged, then the positive electrode will be the active electrode and the negative electrode will serve to complete the circuit. If the ionic substance is negatively charged, then the negative electrode will be the active electrode and the positive electrode will be the indifferent electrode.

In the prior art the polarity of the current source, and thus of the electrodes is fixed. Thus, for a given ionicity, one of the electrodes is always the active electrode, while the other electrode is always the inactive electrode. The active electrode includes a source of the ionic substance, while the indifferent electrode does not. In these prior art devices only one of the electrodes provides a source of the ionic substance. Further, if the electrodes are accidently connected to the wrong terminals of the current source the ionic substance will not be ionotophoresed. Further, in many such devices, if it is discovered that the electrodes have been reversed the device must be removed from the body, the electrodes replaced correctly and then the device must be reapplied.

SUMMARY OF THE INVENTION

It is an object of the invention to provide a iontophoretic device having a means for switching the polarity of the electrodes. The iontophoretic device of the invention includes an electrical current source, at least two electrodes, means for electrically connecting the electrodes to the current source and means for switching the polarity of the electrodes. The switching means may take many forms including a double-pole, double-throw switch, or a digital electronic switching circuit. Preferably the invention includes a timing means for triggering the polarity switching circuit at a preselected time. Preferably there is a ramp circuit which is responsive to the timing means to turn down the current just prior to the time at which the polarity is switched, and to turn up the current after the polarity is switched. Preferably, there is also a means for indicating the polarity of the electrodes such as an indication light. Preferably, both electrodes contain a source of the ionic substance, with one electrode acting as the active electrode when the polarity is in one mode and the other electrode acting as the active electrode when the polarity is in the reverse mode. Thus, twice the amount of ionic substance can be delivered in a single application of the iontophoretic device as compared to previous devices. Further, the invention provides much more flexibility to the operator in choosing the active electrode, correcting errors, etc. even after the device has been applied. Numerous other features, objects and advantages of the invention will become apparent from the following detailed description when read in conjunction with the accompanying drawings.

DESCRIPTION OF THE PREFERRED EMBODIMENT

Figure 1:
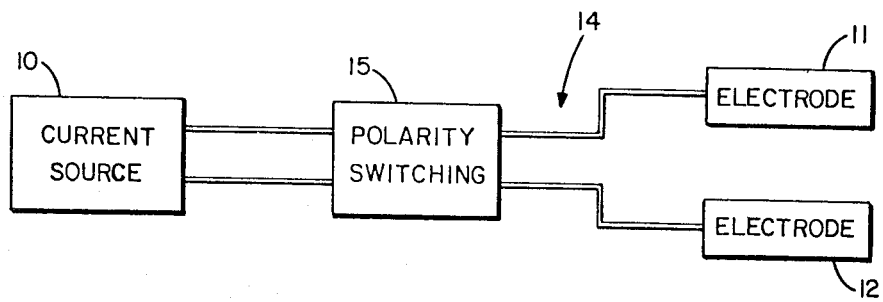
FIG. 1 is a block diagrammatic illustration of an iontophoretic system according to the invention.

A block diagrammatic illustration of the preferred embodiment of the invention is shown in FIG. 1. Current source 10 produces an electric current which is delivered to electrodes 11 and 12 by electrical connecting means 14. A polarity switching means 15 is interposed between the current source and the electrodes and controls their polarity. For example, the polarity may be such that electrode 11 is positively charged and electrode 12 is negatively charged, or the polarity may be reversed so that electrode 11 is negatively charged and electrode 12 is positively charged.

Figure 2:
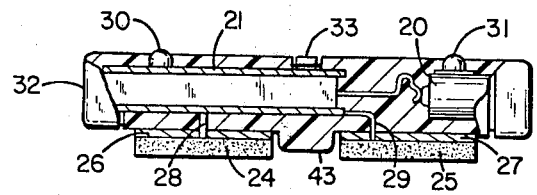
FIG. 2 is partially cut-away side view of an iontophoretic device according to a preferred embodiment of the invention.
Figure 3:
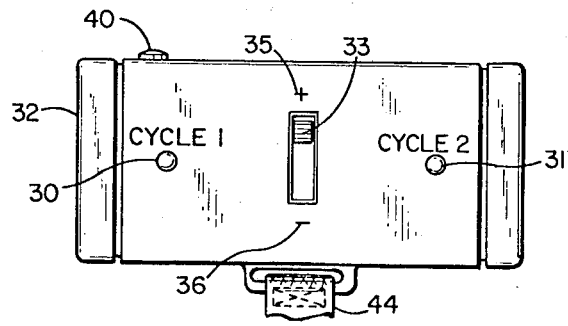
FIG. 3 is a top view of the device of FIG. 2.

FIGS. 2 and 3 show a partially cut-away side view and a top view respectively of an exemplary embodiment of the invention. In this embodiment current source 10 comprises a battery pack 20 and a circuit package 21 for generating and controlling the current. In this embodiment the electrodes 24 and 25 are adhesive pads which contain the ionic substance to be driven into the body. Preferably the pads 24 and 25 comprise an adhesive substance with the ionic substance in admixture therewith. The means for connecting the electrodes 24 and 25 to the current source comprise metal plates 26 and 27, to which the adhesive electrodes 24 and 25 are applied, and leads 28 and 29 which connect the plates to the current generating electronics package 21. Light emitting diodes (LEDs) 30 and 31 which are connected to electronics circuit package 21 and which are visible externally of the casing 32 provide means for indicating which of the electrodes is delivering the ionic substance. Ion switch 33 is electrically connected to circuitry 21 and provides a means for correlating the indicating LEDs 30 and 31 with the electric charge type of the ionic substance. If an ionic substance with a positive charge is to be driven into the tissue with the device then switch 33 is placed in the position towards the plus sign 35. If an ionic substance of a negative charge is to be used, the switch 33 is placed in the direction of negative sign 36. Switch 40 is a on/off switch which is electrically connected to electronic circuitry 21 and activates the iontophoretic device. Projection 43 (FIG. 2) is formed in the center bottom portion of casing 32 to assist in electrically separating electrode pads 24 and 25. Strap 44 (FIG. 3) is provided to assist in attaching the device to a portion of a body to which the device is to be applied, as for example an arm or a leg of a human being.

The device shown in FIGS. 2 and 3 is used by applying the device to the body surface into which it is desired to introduce the ionic substance contained in electrodes 24 and 25. Electrodes 24 and 25 are adhesive and thus will adhere to a body surface, such as skin, holding the device in place. Strap 44 may be used to assist in holding the device in place. If a positive ionic substance has been selected for the iontophoresis process, switch 33 will have been placed in the positive position. When the device is in position, switch 40 is triggered to turn on the device. If the battery has sufficient voltage to operate the device, LED 30 will begin blinking to indicate that the device is operating properly and that electrode 24 beneath LED 30 is delivering the ionic substance. After a preselected time, the device will automatically turn down the current, switch polarity and turn up the current again. LED 31 will then begin blinking to indicate both that the battery life is still sufficient and that the electrode 25 under light 31 is now delivering the ionic substance. After another preselected time the device will shut itself off and light 31 will go out. The time for the switching of polarity and the shutoff time is determined by dosage considerations and the time necessary to deplete the amount of ionic substance stored in the electrodes 24 and 25. Other treatment considerations such as the desire to provide a small dosage over a long period, etc may also impact on the times. In the embodiment shown, LEDs 30 and 31 also indicate whether the device is on the first or the second polarity cycle. It also should be noted that in this embodiment switch 33 also provides a means for manually switching the polarity of the electrodes if it is so desired. In addition, in this embodiment the combination of switch 33 and LEDs 30 and 31 also provide a means for indicating the polarity of the electrodes. That is, if switch 33 is in the plus position when the unit is turned on, then the light that is flashing indicates that the electrode is a positive electrode; and on the other hand if switch 33 is in the negative position when the unit is turned on, then the light flashes above the negtive electrode. The current is turned down prior to the switching of the polarity, then turned up afterwards in order to prevent the unpleasant sensation to the patient which might be caused by the switching of the polarities while the device is operating at maximum current, and at the same time it provides an electronic safety feature.

Figure 4:
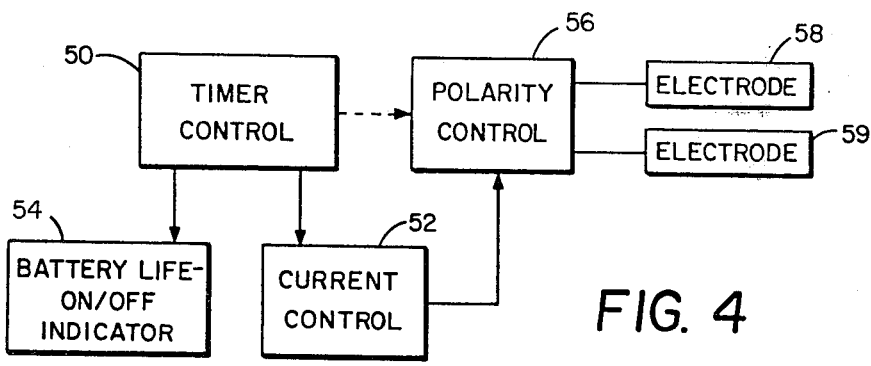
FIG. 4 is a block diagrammatic illustration of the electronic circuitry of a preferred embodiment of the invention.

FIG. 4 shows a block diagrammatic illustration of an exemplary preferred embodiment of the electronics of the invention. The electronics includes a Timing Control Circuit 50, a Current Control Circuit 52, a Polarity Control Circuit 56, Battery Life-ON/OFF Indicator Circuit 54, and electrodes 58 and 59. The turning on of the on/off switch 46 (not shown in FIG. 4) activates circuits 50, 52, 54 and 56. Timer control circuit 50 provides a signal to Battery Life-ON/OFF Indicator Circuit 54 which, in turn, activates an indicating device, such as LEDs 30 and 31 in FIG. 3, provided the battery voltage is above a predetermined level which is considered to be sufficient to reliably operate the device. Timer Control Circuit 50 also provides a signal to Current Control Circuit 52. Current Control Circuit 52 responds to the signal to ramp on the iontophoretic current; that is, the iontophoretic current is turned on gradually from a zero value up to the full current value. This prevents burnings, prickings, or other unpleasant sensations when the current is turned on. The iontophoretic current produced by Current Control Circuit 52 is applied to electrodes 58 and 59 through Polarity Control Circuit 56. Polarity Control Circuit 56 determines the direction in which the current flows between electrodes 58 and 59, and thus controls which of the electrodes is the active electrode. The switching of the polarity may be either manually by means of an external switch (not shown in FIG. 4) or automatically by circuit 56 in response to a signal from Timing Control Circuit 50 as shown by the dotted arrow.

The dosage of the ionic substance which is applied to the body is controlled by Timer Control Circuit 50 and Current Control Circuit 52. Current Control Circuit 52 provides a constant current output to the electrodes 58 and 59 which is independent of the load within the power supply limits, which load is generally skin impedance. Thus, the amount of ionic substance driven into the body by the current will be constant in time. In this manner, control of the time over which of the current is applied controls the dosage. After a predetermined amount of time, Timing Control Circuit 50 applies a second signal to Current Control Circuit 52 which causes the Current Control Circuit to ramp the iontophoretic current down. Again, the ramping is to prevent any unpleasant affects. Alternatively, the dosage may be controlled manually by turning off the on/off switch (not shown in FIG. 4) at a chosen time.

In the embodiments in which the polarity is controlled manually, the polarity may be switched after the Timing Control Circuit ramps down the current. In embodiments where the polarity control is automatic, a timing signal to the Polarity Control Circuit 56 will switch the polarity automatically after the current is ramped down. After the polarity is switched, the current may be turned back on either by the manual on/off switch or, in the case of the automatically controlled embodiments, by a timing signal to Current Control Circuit 52 which causes the current to ramp up again. After a second predetermined time, a further signal from Timing Control Circuit 50 to Current Control Circuit 52 again causes the current to ramp down and the device to turn itself off. Signals from Timing Control Circuit 50 to the Battery Life-ON/OFF indicator 54 cause the indicator LEDs to go off each time the circuit is ramped down, and in the automatic embodiments to indicate which electrode is the active electrode.

In general, it should be noted that the word ramping does not necessarily indicate that the current is turned completely off or is turned down or up with any specific rate; it refers to a turning down or up of the current in a manner that will prevent injury or unpleasantness etc.

Figure 5:
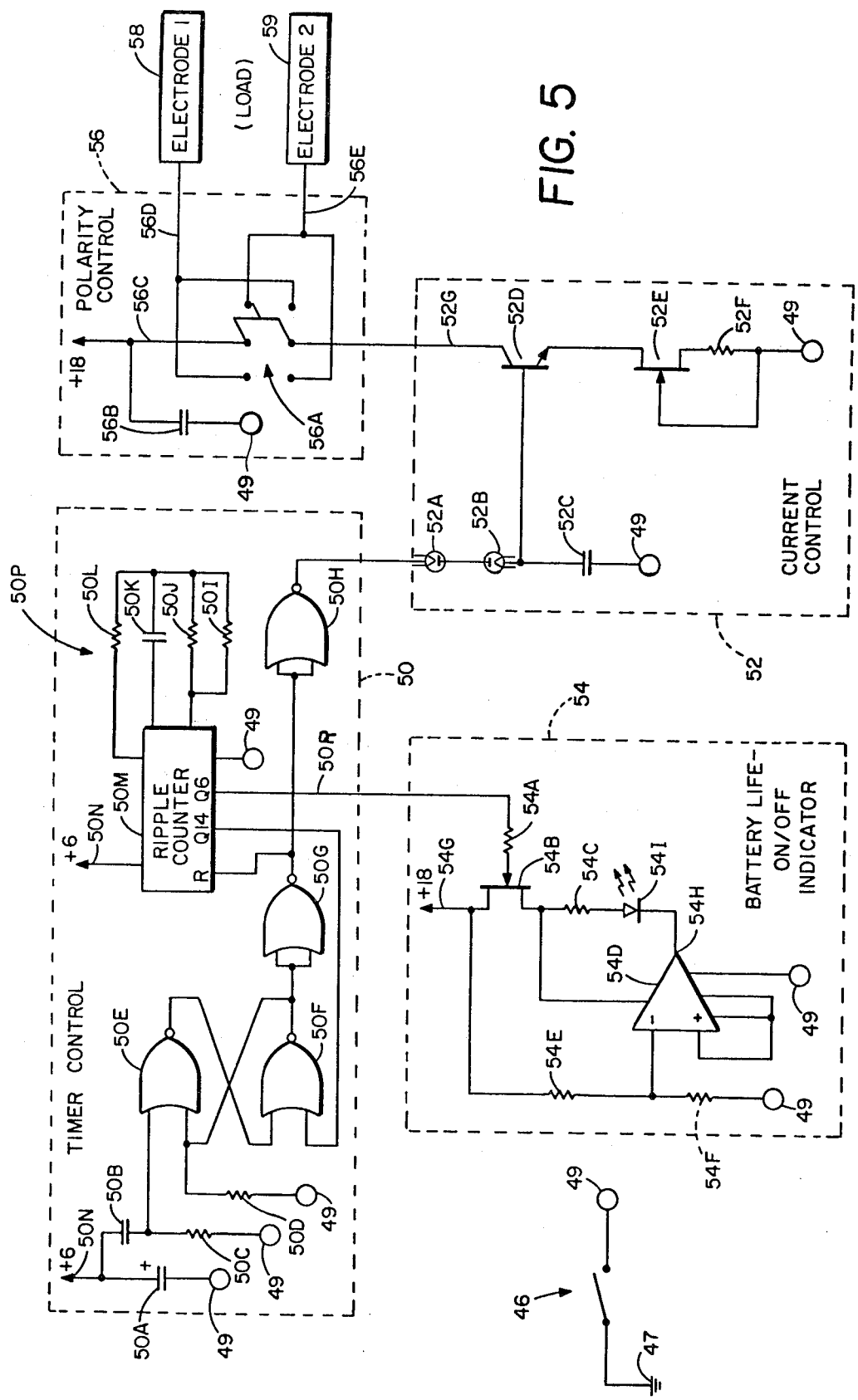
FIG. 5 is a more detailed electronic diagram of the circuitry according to a preferred embodiment of the invention.

A more detailed electronic diagram of an exemplary embodiment of the invention is shown in FIG. 5. The circuit is arranged so that the individual subcircuits 50, 52, 54 and 56 occupy approximately the same relative positions as they do in FIG. 4. On/off switch 46 connects ground 47 and an input line which connects each of the subcircuits at the points indicated by an open circle, such as circle 49 indicated at the bottom of Battery Life-ON/OFF Indicator Circuit 54.

Figure 6:
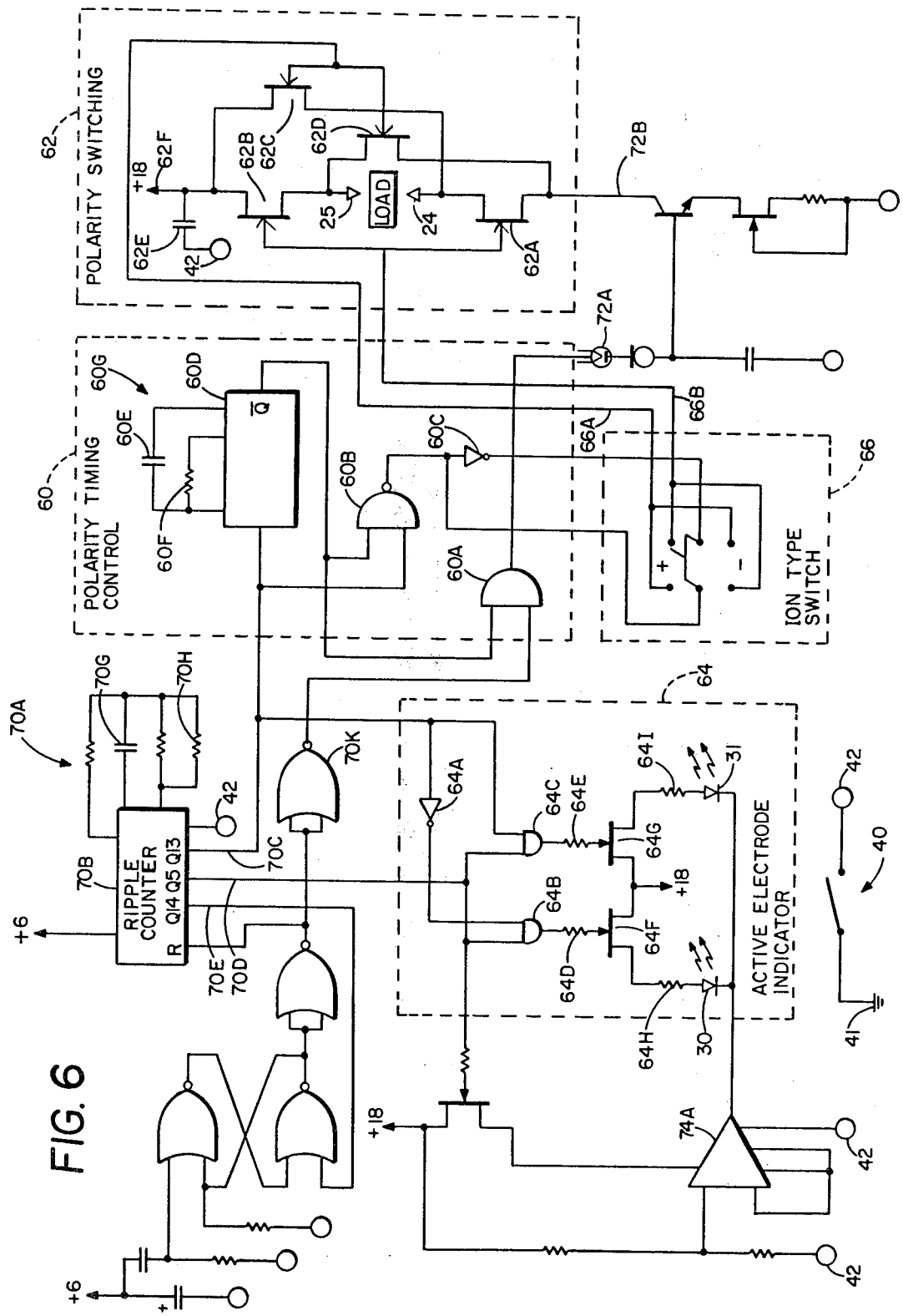
FIG. 6 is a detailed electronic diagram of an alternative preferred embodiment of the invention.

The electronic circuits of FIGS. 5 and 6 include NOR gates, AND gates, a NAND gate, inverters, and one monostable multivibrator or one-shot. These elements are shown by their conventional symbols, a NOR gate being shown at 50E in FIG. 5, an AND gate being shown at 60A in FIG. 6, the NAND gate being shown at 60B in FIG. 6, an inverter being shown at 64A in FIG. 6, and the one-shot or monostable being shown at 60D in FIG. 6. As is well known in the literature, a NOR gate is an electronic device with one output and two or more inputs. If either one of the inputs to a NOR gate is the positive circuit voltage (6 volts in the case of the present circuit) conventionally referred to as a logic "1" state, then the output of the NOR gate is the ground voltage, conventionally referred to as the logic "0" voltage. If all inputs are to the logic "0" state, then the signal at the output is a logic "1" state. An AND gate has two or more inputs and one output. The output of an AND gate is a logic "0" signal unless the signals applied to the inputs are all a logic "1" in which case the output of the AND gate is a logic "1" signal. A NAND gate also has two or more inputs and one output. The output of a NAND gate is a logic "1" signal unless the signal applied to all of the inputs is a logic "1", in which case the output is a logic "0" signal. An inverter has one input and one output, with the output providing a signal having a logic value opposite to that of the signal applied to the input. The conventional provisions of power supply voltages and ground voltages to the gates, inverters, and flip-flop are not shown.

Timer Control Circuit 50 (FIG. 5) comprises 33 microfarad capacitor 50A, 0.1 microfarad capacitor 50B, 1 megohm resistors 50C and 50D, NOR gates 50E through 50H, 910 kilohm resistor 50I, 560 kilohm resistor 50J, 0.056 microfarad capacitor 50K, 3.3 megohm resistor 50L and ripple counter 50M.

Capacitor 50A is connected between the line 49 to on/off switch 46 and the positive 6 volt voltage terminal 50N. This is a filter capacitor whose purpose is to reduce circuit noise, and is not otherwise actively involved in the timing control function. Capacitor 50B is connected between the high voltage side of capacitor 50A and the upper input terminal to NOR gate 50E, which terminal is also connected to ground input line 49 through resistor 50C. NOR gates 50E and 50F are coupled in a standard configuration for a flip-flop circuit. That is, the output of NOR gate 50E is connected to the upper input of NOR gate 50F, while the output of NOR gate 50F is connected to the lower input to gate 50E. The lower input to gate 50F is connected to the Q14 counter (No. 3 pin) output of ripple counter 50M. The output of NOR gate 50F is also connected to the two inputs of NOR gate 50G. The lower input of gate 50E is also connected to ground input line 49 through resistor 50D. The output of NOR gate 50G is connected to the reset input (No. 12 pin) of ripple counter 50M and also to both inputs of NOR gate 50H. Resistors 50I and 50J are connected in parallel between the No. 10 pin of ripple counter 50M and one side of capacitor 50K, which is also connected through resistor 50L to the No. 11 pin of ripple counter 50M. The other side of capacitor 50K is connected to the No. 9 pin of ripple counter 50M. The No. 8 pin of ripple counter 50M is connected to ground input 49 while the No. 16 pin is connected to the +6 volt power supply 50N. Ripple counter 50M is a CD4060 ripple counter divider available from RCA Solid State Division, Box 3200, Summerville, N.J. 08876. The output of NOR gate 50H is applied to Current Control Circuit 52 which will be described below.

When switch 46 is closed the inputs to NOR gate 50G will be at a logic "0" since they are connected to ground through resistor 50D, and no current is initially flowing in the line. The output of gate 50G will thus be a logic "1" which resets ripple counter 50M, setting the Q14 output to a logic "0", and thus the lower input to gate 50F to a logic "0". At the same time a current will begin flowing in the circuit from positive terminal 50N through resistor 50C to ground (charge will be building on capacitor 50B) which will set the upper terminal to NOR gate 50E at a logic "1". The output of gate 50E is thus forced to a logic "0" which is applied to the upper input of gate 50F. The two inputs to gate 50F being a logic "0", the output will switch to a logic "1". This causes the output of gate 50G to go to a logic "0", which releases the reset on ripple counter 50M, which permits it to begin counting, and at the same time causes the output of gate 50H to switch from a logic "0" to a logic "1". While ripple counter 50M is counting the upper input to NOR gate 50E falls to a logic "0", however the output of the gate is maintained at a logic "0" because the lower input to the gate is held at a logic "1" as long as the lower input of gate 50F is held to a logic "0".

Ripple counter 50M is driven by oscillator circuit 50P consisting of resistors 50I, 50J, 50L and capacitor 50K. The value of resistor 50I is selected so that the oscillation period is 36.6 milliseconds. The ripple counter will count the 36.6 millisecond oscillations so that within approximately 5 minutes its fourteenth counter is triggered, and the Q14 pin goes to a logic "1". This logic "1" signal applied to the lower input of gate 50F causes the output of the gate to go to a logic "0", which in turn forces the output of gate 50G to a logic "1", which holds ripple counter 50M reset and changes the output of NOR gate 50H to a logic "0". The logic "0" output of NOR gate 50F is also applied to the lower input of NOR gate 50E. Both inputs of NOR gate 50E being a logic "0", the output will become a logic "1", which is applied to the upper input of NOR gate 50F forcing its input to a logic "0" thereby latching gates 50E and 50F in the "off" state such that the output of NOR gate 50H remains a logic "0" until switch 46 is turned off, and then on again to restart the cycle. Thus, Timer Control Circuit 50 provides a logic "1" signal to Current Control Circuit 52 for a 5-minute period after switch 46 is turned on. While counter 50M is counting up to five minutes, its sixth counter stage will go to a logic "1" approximately every 2.3 seconds. The output of the sixth counter stage (No. 4 pin) will thus go to a logic "1" for a 1.15 second period every 2.3 seconds. This signal is passed to Battery Life-ON/OFF Indicator Circuit 54 and used as discussed below. When the counter has fully counted the five minutes and gates 50E and 50F are latched into the "off" state all counter outputs will be at a logic "0" thus holding the various subcircuits in an off position as will be further described below.

Current Control Circuit 52 includes two constant current 1N 5290 diodes 52A and 52B, 330 microfarad capacitor 52C, a 2N 2222 transistor 52D, a 2N 4341 FET 52E, and 510 kilohm resistor 52F.

The anode of constant current diode 52A is connected to the output of NOR gate 50H in Timer Control Circuit 50. The cathode of diode 52A is connected to the cathode of diode 52B while the anode of diode 52B is connected to one side of capacitor 52C and also to the base of transistor 52D. The other side of capacitor 52C is connected to ground input line 49. The emitter of transistor 52D is connected to the drain of FET 52E. The gate of FET 52E is connected to ground input line 49 and is also connected to its own source through resistor 52F. The collector of transistor 52D is connected to output line 52G which is the input to Polarity Control Circuit 56.

When Timer Control Circuit 50 causes NOR gate 50H to go to a logic "1" state after switch 46 is turned on, a 6 volt signal is applied to the anode of diode 52A. Since this is a constant current diode the current that passes through it is fixed and thus the charge on capacitor 52C is built up slowly, over a period of about 1 second. Thus, the voltage applied to the base of transistor 52A builds up slowly, to the full 6 volt value over the same period, causing the transistor to turn on slowly over the same period. FET 52E and resistor 52F form a conventional current-limiting circuit. Resistor 52F is chosen to limit the current to 2 milliamps. Thus, upon application of the signal from Timer Control Circuit 50, Current Control Circuit 52 slowly, over a period of about a second, ramps up the current through its output line 52G from 0 to a maximum constant current of 2 milliamps. When, at the end of the 5-minute period, the signal from Timer Control Circuit 50 drops to a logic "0", the charge on capacitor 52C will slowly drain through current-limiting diode 52B, again over about a 1-second period. Thus, the transistor 52D will be slowly turned off over the same period and the current through the output line 52G will slowly ramp down to a 0 value.

Battery Life-ON/OFF Indicator Circuit 54 comprises 100 kilohm resistor 54A 2N4338 FET 54B, 1.5 kilohm resistor 54C, LED 54I, an LM10H differential amplifier 54D, which is available from National Semiconductor Corp. at 2900 Semiconductor Drive, Santa Clara, CA 95051, 820 kilohm resistor 54E and 12 kilohm resistor 54F. The gate of FET 54B is connected to the Q6 output (No. 4 pin) of ripple counter 50M in Timer Control Circuit 50 through resistor 54A. The drain of FET 54B is connected to the positive 18 volt power source 54G and to ground input line 49 through resistors 54E and 54F. The source of FET 54B is connected to the output 54H (No. 6 pin) of amplifier 54D through resistor 54C and LED 54I, and is also connected to the No. 7 pin of amplifier 54D. The negative input terminal (No. 2 pin) of amplifier 54D is connected to the line between resistors 54F and 54E. The positive input terminal (No. 3 pin) of amplifier 54D is connected to both the No. 1 pin and No. 8 pin of the same amplifier. The No. 4 input pin of the amplifier 54E is connected to ground input line 49.

As discussed above, the Q6 output of ripple counter 50M in Timer Control Circuit 50 will go to a logic "1" for a 1.15 second period once each 2.3 seconds while the counter is running. Each time it goes to a logic "1" FET 54B is turned on for the 1.15 second period provided the battery level is above the predetermined level which for this embodiment is 14 volts. The circuit consisting of amplifier 54D, resistors 54C, 54E and 54F and LED 54I is a conventional battery-level test circuit disclosed in the applications manual for the LM10H amplifier published by National Semiconductor Corporation.

When FET 54B turns on, it activates amplifier 54D which compares the voltages between its negative and positive inputs. If the battery charge is higher than 14 volts the amplifier connects its No. 6 pin output terminal 54H to ground line 49. If switch 46 is closed this will close the circuit from the positive terminal 54G to ground 47 through LED 54I, causing the LED to operate. If the battery voltage is below 14 volts, amplifier 54D will not connect output 54H to ground and LED 54I will not turn on. Thus, Battery Life-ON/OFF Indictor Circuit 54 will cause LED 54I to blink at 2.3 second intervals during the 5-minute period when the current is on, providing the battery level is above 14 volts.

Polarity Control Circuit 56 comprises double-pole, double-throw switch 56A and 33 microfarad capacitor 56B. Capacitor 56B plays no essential part in the polarity control function, but is simply a filter capacitor which is connected between the ground and input line 49 and the positive voltage input 56C. One pole of switch 56A is connected to the positive 18 volt power supply through line 56C and the other pole is connected to the input line 52G from Current Control Circuit 52. The upper terminal of the left throw and the lower terminal of the right throw of switch 56A are connected to output line 56D which goes to electrode 1. The lower terminal of the left throw and the upper terminal of the right throw of switch 56A are connected to output line 56E to electrode 2. Thus, if switch 56A is in the left hand throw position, electrode 1 will have positive polarity while electrode 2 will have a negative polarity and current will flow from electrode 1 to electrode 2. If the ionic substance to be driven into the tissue is a positive ion, electrode 1 will be the active electrode when switch 56A is in the left hand position, while if the ionic substance is a negative ion, then electrode 2 will be the active electrode. When switch 56A is in the right hand throw position the polarity, direction of current flow of the electrodes is reversed.

In the embodiment shown in FIG. 5, switch 56A is a manual switch accessible from the exterior of the casing, such as 33 in FIG. 3, of the iontophoretic device. If appropriate markings are placed on the case, the position of the switch will provide an indication of the polarity of the electrodes. If the ionicity of the ionic substance is known, then the switch may also act as a means for indicating the active electrode.

An iontophoretic device employing the circuitry of FIG. 5 may be used by turning the device on, allowing the ionic substance from one electrode to be delivered, and then after the device turns itself off, manually reversing the polarity and turning the device on again so the second electrode will deliver its ionic substance. In this manner both electrodes may be used to deliver the ionic substance, and twice the amount of ionic substance can be delivered per application of the iontophoretic device.

FIG. 6 shows a detailed electronic diagram of another exemplary preferred embodiment of the invention. This is a more highly automated circuit than the circuit shown in FIG. 5 and includes Polarity Timing Control Circuit 60 which provides additional timing functions connected with the polarity switching, Polarity Switching Circuit 62 which responds to signals from the timing circuits to automatically switch the polarity, Active Electrode Indicator Circuit 64 which automatically indicates which electrode is the active electrode, and Ion Type Switch 66 which changes the polarity of the electrodes so that the Active Electrode Indicator Circuit 64 will properly indicate the active electrodes with both types of ionic substances.

The circuitry of FIG. 6 is the circuitry employed in embodiment of the iontophoretic generator shown in FIGS. 2 and 3.

The portions of the circuitry of FIG. 6 not forming part of circuits 60, 62, 64 and 66 is the same as the circuitry just described in connection with FIG. 5, except for the portion associated with ripple counter 70B. This latter portion differs from the circuit of FIG. 5 in that the value of capacitance 70G in the oscillator circuit 70A is chosen to be 0.1 microfarads and resistor 70H is selected so that the oscillation of circuit 70A will have a period of 73.2 milliseconds, and an additional output 70C is added to ripple counter 70B at the terminal of the thirteenth counter (No. 2 pin). In addition, output 70D which drives the LEDs in Active Electrode Indicator Circuit 64, is connected to the fifth output stage (No. 5 pin) rather than the sixth output stage. With these changes, output line 70C will become a logic "0" after switch 40 is turned on, then after a 5-minute period it will become a logic "1" and will remain at that state for a 5-minute period. Output line 70D will go to a logic "1" for a 1.15 second period every 2.3 seconds while the counter is running, just as the corresponding output 50R in FIG. 5. Output line 70E will become a logic "0" when the switch 40 is turned on and will go to a logic "1" approximately 10 minutes after the initiation of the counter. Thus the counter 70B in FIG. 6 will provide a signal through line 70C to the Polarity Timing Control Circuit that is a logic "0" for the first five minutes after the device is turned on and a logic "1" for the next five minutes. Output 70D will provide the same timing signal to the LED indicators in circuit 64 as the corresponding line 50R in FIG. 5. As can be seen from considering the discussion of the operation of NOR gates 50F, 50G and 50H in the discussion of FIG. 5, the signal from line 70E will cause NOR gate 70K to provide a signal to the Polarity Timing Control Circuit that becomes a logic "1" for a 10-minute period after switch 40 is turned on, and then becomes a logic "0".

Polarity Timing Control Circuit 60 comprises AND gate 60A, NAND gate 60B, inverter 60C, monostable multivibrator 60D, capacitor 60E and resistor 60F. Multivibrator 60D is a conventional one-shot type circuit such as the RCA-CD4047A available from RCA Solid State Division, Box 3200, Summerville, N.J. 08876. Capacitor 60E is connected between pin 3 and pin 1 of multivibrator 60D and resistor 60F is connected between pin 3 and pin 2. The values of capacitor 60E and resistor 60F are chosen so as to provide an approximately 1 second decay period ($T_n$) for the monostable vibrator 60D according to the formula $T_n = 2.48RC \approx 1$ second.

Ripple counter output 70C is applied to the positive edge trigger input of monostable multivibrator 60D and the lower input of NAND gate 60B in Polarity Timing Control Circuit 60. The $\overline{Q}$ output of multivibrator 60D is applied to the upper input of NAND gate 60B and also to the upper input of AND gate 60A. The lower input of AND gate 60A is provided by the output of NOR gate 70K as discussed above. The output of NAND gate 60B is connected to one of the poles of switch 66 and is also provided as an input to inverter 60C. The output of inverter 60C is provided to the other of the poles of switch 66. The output of AND gate 60A is provided to the anode of constant current diode 72A which corresponds to the constant current diode 52A in the Current Control Circuit of FIG. 5.

From the above connections it can be seen that when switch 40 is turned on a logic "0" signal is applied to NAND gate 60B. The output of NAND gate 60B will thus become a logic "1". The logic "0" signal from output 70C applied to the clock input of multivibrator 60D causes the $\overline{Q}$ output to become a logic "1". At the same time, the output of NOR gate 70K will become a logic "1", and thus both inputs to AND gate 60A will be a logic "1", causing its output to become a logic "1" immediately after switch 40 is turned on. This signal will initiate the ramp up of the current as discussed above in relation to FIG. 5. After a 5-minute period output line 70C goes to a logic "1", which causes the $\overline{Q}$ output of multivibrator 60D to become a logic "0". This logic "0" applied to AND gate 60A causes its output to become a logic "0" which causes the current to ramp down as discussed above in relation to FIG. 5. The logic "0" signal from the $\overline{Q}$ output of multivibrator 60D also is applied to the upper input of NAND gate 60B which causes its output to remain at logic "1". After a 1-second interval, after which the current in the Current Control Circuit is fully ramped down to zero, monostable multivibrator 60D times out and the $\overline{Q}$ output returns to a logic "1". Now, since both inputs to NAND gate 60B are now a logic "1" its output becomes a logic "0" which switches the polarity of the electrodes, in a manner which shall be described below in the discussion of circuit 62. At the same time the logic "1" signal from the $\overline{Q}$ output of the multivibrator 60D causes the output of AND gate 60A to return to a logic "1" which again causes the current to ramp up to its full value. After another 5-minute interval (10 minutes after the device was turned on) the output of NOR gate 70K becomes a logic "0" which causes the output of AND gate 60A to become a logic "0" which again ramps down the current. At the same time the logic "1" on output 70E of counter 70B causes the counter to be reset which turns the counter and indicators off as discussed in relation to FIG. 5.

Ion switch 66 consists of a double-pole, double-throw switch. Its right and left hand poles are connected to outputs of NAND gate 60B and inverter 60C as discussed above. Its upper left throw and lower right throw are connected to output line 66A, while its lower left throw and upper right throw are connected to output line 66B. Because of inverter 60C, the poles of switch 66 will always be in opposite logic states when the device is operating. Thus, output lines 66A and 66B will also be in opposite logic states, whether the switch 66 is in its upper throw position or its lower throw position. As can be seen from the connections discussed above, the action of the switch will be to reverse the signals on lines 66A and 66B.

Polarity switching circuit 62 comprises FETs 62A, 62B, 62C and 62D and 33 microfarad capacitor 62E. Capacitor 62E does not perform an active role in the polarity switching circuit, but is a filter capacitor which is connected and functions as the corresponding capacitor 56B in FIG. 5. The gates of FETs 62A and 62B are connected to the output line 66B from ion type switch 66. The gates of FETs 62C and 62D are connected to output line 66A from the same switch. The source of FET 62A is connected to the output line 72B from the Current Control Circuit, while the drain is connected to the output to electrode No. 2 (24). The source of FET 62B is connected to the output to electrode No. 1 (25) while its drain is connected to the +18 volt power supply. The drain of FET 62C is also connected to the +18 volt power supply while its source is connected to the output line to electrode No. 24. The drain of FET 62D is connected to the output line to electrode No. 25, while its source is connected to the current output line 72B.

If ion type switch 66 is in the upper (positive) throw position, then during the first 5 minutes of operation of the device, line 66A will be in a logic "1" state while line 66B will be in a logic "0" state. The logic "0" signal applied to the gates of FETs 62A and 62B will keep these FETs turned off, while the logic "1" signal applied to the gates of FETs 62C and 62D will turn these FETs on. Current will thus flow from the +18 volt voltage source through FET 62C to electrode No. 2(24). If the electrodes are applied to tissue the current will flow through the tissue and then through electrode 1 (25) and FET 62D back through current input line 72B. Thus, if ion type switch is in the positive position, which means the ionic substance is positive, electrode 24 will be the active electrode and electrode 25 will be the negative electrode during the first 5-minute cycle. After the first five minutes, the signal from NAND gate 60B will reverse, and the signals from lines 66A and 66B will also reverse, causing FETs 62A and 62B to turn on and FETs 62D and 62C to turn off. Current will now flow from positive input 62F through FET 62B to electrode 25, through the tissue and to electrode 24, and through FET 62A to current line 72B. Thus, during this 5-minute period, electrode 25 will be the active electrode. If the ionic substance is negative, ion type switch will be placed in the down (negative) position and the directions of the currents will be reversed in the two cycles. Since the sign of the ionic substance is also reversed, electrode 24 will still be the active electrode during the first cycle and electrode 25 will still be the active electrode during the second cycle.

Turning attention to the Active Electrode Indicator Circuit 64, this circuit comprises inverter 64A, AND gates 64B and 64C, 100 kilohm resistors 64D and 64E, No. 2N4338 FETs 64F and 64G, 1.5 kilohm resistors 64H and 64I, and LEDs 30 and 31. Line 70D from counter 70B is connected to one of the inputs of gates 64B and 64C. Output 70C from counter 70B is connected to one of the inputs of gate 64C and through inverter 64A to one of the inputs of gate 64B. The output of gate 64B is connected through resistor 64D to the gate of FET 64F, while the output of gate 64C is connected through resistor 64E to the gate of FET 64G. The drains of FETs 64F and 64G are connected to the +18 volt power source. The source of FET 64F is connected through resistor 64H and LED 30 to the output (No. 6 pin) of amplifier 74A. Likewise, the source of FET 64G is connected through resistor 64I and LED 31 to the output of amplifier 74A.

As can be seen from the connections above, immediately after switch 40 is turned on line 70C will be a logic "0" and thus the right input to AND gate 64B will be logic "1" while the right input to AND gate 64C will be a logic "0". The logic "0" signal on AND gate 64C will hold its output to a logic "0", thus holding FET 64G in the off condition. As counter 70B begins to count, line 70D will go to a logic "1" and return to a logic "0" over a 2.3 second period as discussed above. During the time it is a logic "1" both the inputs to AND gate 64B will be a logic "1" and thus, its output will go to a logic "1", turning FET 64F on and allowing current to flow through LED 30, as was described earlier in connection with FIG. 5. At the times in which line 70D goes to a logic "0" the output of gate 64B will return to a logic "0" turning off FET 64F and LED 30. Thus, during the first 5-minute cycle, LED 30 will blink at the rate discussed above. During the second 5-minute cycle line 70C goes to a logic "1" which holds the output of gate 64B at a logic "0" state holding FET 64F off, at the same time permitting the output from gate 64C to oscillate between the logic "0" and logic "1" states, alternately turning on and off FET 64G, causing LED 31 to alternately turn on and off. Thus, during the second 5-minute cycle LED 31 will blink. As can be seen from comparing the operation of the Polarity Switching Circuit 62 and ion type switch 66 discussed above, LED 30 will blink while electrode 24 is the active electrode, while LED 31 will blink while electrode 25 is the active electrode.

There has been described a novel apparatus that provides for double the amount of iontophoretic substance to be delivered in a single application of an iontophoretic device, and provides for an indication of which electrode is the active electrode, and thus provides for a more efficient and flexible iontophoretic process. While the invention has been described in connection with two particular embodiments, one skilled in the art will appreciate that numerous other embodiments and departures from the embodiments shown may be made without departing from the inventive concepts. For example, a wide variety of different characteristic times can be selected by altering the oscillation circuits 50P, 60G, and 70A, or variable resistances be inserted in these circuits to allow the different characteristic times to be varied. Or different types of counters may be substituted for counters 50M and 70B in order to provide different varieties of timing sequences. Or microprocessors can be incorporated for functions such as automatic power up and down as well as controlling the timing for daily dosage delivery. Different currents and voltages can be selected by altering the current control circuits such as 52, as for example resistor 52F can be replaced by a potentiometer so that the current applied can be externally varied or skin-electrode impedance can be monitored to control the output current. Switching means 56A, 66 and 62 may be replaced by many other types of switching means.

Instead of using two LEDs to indicate the two cycles, one LED could be used, and it could be made to blink at different rates for each of the cycles. Or, alternatively, many other indicating means could be used. Many other equivalent electronic circuits may be substituted for the circuits described, and within the circuits many substitutions and additions can be made. For example, resistor 54A could be eliminated and a larger resistor value could be substituted for resistor 54E to form an equivalent circuit. Many additional features, and controls can be added to the electronic circuitry while still employing the inventive elements. Those skilled in the art will see many other variations than those described above.

What is claimed is:

1. An iontophoretic device comprising:
   a source of electrical current;
   first electrode means for containing a charged ionic substance for delivery to said body;
   second electrode means for containing said charged ionic substance for delivery to said body;
   timing means coupled to said source of electrical current for timing a first period and a second period; and
   polarity switching means coupled to said timing means, said source of electrical current and said first and second electrode means for applying said electrical current across said first and second electrode means in a first direction to effect delivery of said ionic substance contained in one of said first and second electrode means during said first period and for applying said electrical current across said first and second electrode means in a second direction to effect delivery of said ionic substance contained in the other of said first and second electrode means during said second period.

2. An iontophoresis device according to claim 1 further including indicator means for indicating which of said first and second electrode means is delivering said charged ionic substance to said body.

3. An iontophoresis device according to claim 1 further comprising cycle indicator means for indicating the duration of said first and second periods.

4. An iontophoresis device according to claim 3 wherein said cycle indicator means further indicates which of said first and second electrode means is delivering said charged ionic substance to said body.

5. An iontophoresis device according to claim 3 further comprising ion type switch means settable to a positive and to a negative setting, coupled to said timing means and to said polarity switching means, for determining said first and second directions of current flow during said first and second periods such that when said ion switch means is set to said positive setting said first electrode is positively charged relative to said second electrode means during said first period and said second electrode means is positively charged relative to said first electrode means during said second period, and such that when said ion type switch means is set to said negative setting, said first electrode means is negatively charged relative to said second electrode means during said first period and said second electrode means is negatively charged relative to said first electrode means during said second period whereby when said ion type switch means is set corresponding to the charge of said charged ionic substance, said cycle indicator means also indicates which of said first and second electrode means is delivering said charged ionic substance to said body.

6. An iontophoresis device according to claim 3 further comprising:
   ion type switch means for correlating said first and second directions of current flow to the charge of said ionic substance such that said cycle indicator means also indicates which of said first and second electrode means is delivering said charged ionic substance to said body.

7. A device for iontophoretic introduction of an ionic substance into tissue, comprising an electrical current source, at least two electrodes each including a source of said ionic substance, means for electrically connecting the electrodes and current source, means for switching the polarity of said electrodes, and means for ramping down said current prior to the switching of polarity and for ramping up said current after the switching of polarity.

8. A device as described in claim 7 and further comprising:
   timing means for providing at least one timing signal; and
   wherein said means for switching comprises a means responsive to said timing signal for switching the polarity at a preselected time.

9. A device for iontophoretic introduction of an ionic substance into tissue, comprising an electrical current source, at least two electrodes each including a source of said ionic substance, means for electrically connecting the electrodes and the current source, means for switching the polarity of said electrodes, and a means for indicating which of said electrodes is delivering said ionic substance, and further including an ion switch means for correlating said indicating means with the electric charge type of said ionic substance.

10. An iontophoresis device, comprising:
    a source of electrical current;
    a first electrode means for containing a charged ionic substance for delivery to a body;
    a second electrode means for containing said charged ionic substance for delivery to said body;
    control means coupled to said first and second electrode means and to said source of electrical current for applying said electrical current across said first and second electrode means in a first direction to deliver said charged ionic substance contained in said first electrode means to said body and in a second direction to deliver said charged ionic substance contained in said second electrode means to said body; and
    active electrode indicator means for indicating which of said first and second electrode means is delivering said charged substance to said body.

11. An iontophoresis device according to claim 10 wherein said control means comprises:
    polarity switching means for reversing the direction of electrical current applied across said first and second electrode means, switchable to either a first state or a second state;
    ion type switch means coupled to said polarity switching means, switchable to either a positive or a negative setting, for determining said first and second directions of current flow such that when said ion type switch means is switched to said positive setting, said first electrode means is positive relative to said second electrode means when said polarity switching means is switched to said first state and said first electrode means is negative relative to said second electrode means when said polarity switching means is switched to said second state, and such that when said ion type switch means is switched to said negative setting, said first electrode means is negative relative to said second electrode means when said polarity switching means is switched to said first state and said first electrode means is positive relative to said electrode means when said polarity switching means is switched to said second state; and
    wherein said active indicator means provides a first indication associated with said first electrode means when said polarity switching means is switched to said first state, and provides a second indication associated with said second electrode means when said polarity switching means is set to said second state, whereby when said ion type switch means is set corresponding to the charge of said charged ionic substance, said active electrode indicator means indicates which of said first and second electrode means is delivering said charged substance to said body.

12. An iontophoresis device according to claim 11 wherein said control means further comprises timing means, coupled to said polarity switching means for switching said polarity switching means to said first state during a first time period and for subsequently switching said polarity switching means to said second state for a second time period.

13. An iontophoresis device according to claim 12 wherein said control means further comprises ramping means responsive to said timing means for gradually reducing the magnitude of said electrical current applied across said first and second electrode means prior to the expiration of said first period and for gradually increasing the electrical current applied across said first and second electrode means subsequent to the initiation of said second period.

* * * * *